United States Patent
Gandhi et al.

(10) Patent No.: US 9,585,389 B2
(45) Date of Patent: Mar. 7, 2017

(54) MICROBICIDAL COMPOSITION

(71) Applicants: Dow Global Technologies LLC, Midland, MI (US); Rohm and Haas Company, Philadelphia, PA (US)

(72) Inventors: Usha Gandhi, Hatboro, PA (US); Christine McInnis, Blue Bell, PA (US); Kiran Pareek, Bensalem, PA (US); Paul O. Schook, Lake Zurich, IL (US); Nigel G. Watson, Chadds Ford, PA (US); Terry Michael Williams, Lower Gwynedd, PA (US); Bei Yin, Phoenixville, PA (US)

(73) Assignees: DOW GLOBAL TECHNOLOGIES LLC, Midland, MI (US); ROHM AND HAAS COMPANY, Philadelphia, PA (US)

( * ) Notice: Subject to any disclaimer, the term of this patent is extended or adjusted under 35 U.S.C. 154(b) by 0 days.

(21) Appl. No.: 15/026,126

(22) PCT Filed: Oct. 2, 2014

(86) PCT No.: PCT/US2014/058819
§ 371 (c)(1),
(2) Date: Mar. 30, 2016

(87) PCT Pub. No.: WO2015/051115
PCT Pub. Date: Apr. 9, 2015

(65) Prior Publication Data
US 2016/0219875 A1 Aug. 4, 2016

Related U.S. Application Data

(60) Provisional application No. 61/886,332, filed on Oct. 3, 2013.

(51) Int. Cl.
| | | |
|---|---|---|
| *A01N 31/16* | (2006.01) |
| *A61K 31/765* | (2006.01) |
| *A01N 31/14* | (2006.01) |
| *A01N 25/30* | (2006.01) |
| *A01N 31/02* | (2006.01) |
| *C02F 1/50* | (2006.01) |

(52) U.S. Cl.
CPC ............. *A01N 31/14* (2013.01); *A01N 25/30* (2013.01); *A01N 31/02* (2013.01); *C02F 1/50* (2013.01); *C02F 2303/04* (2013.01); *C02F 2305/04* (2013.01)

(58) Field of Classification Search
CPC .............................. A01N 31/14; A61K 31/80
USPC ........................ 514/718; 424/78.37
See application file for complete search history.

(56) References Cited

U.S. PATENT DOCUMENTS

| | | |
|---|---|---|
| 4,295,932 A | 10/1981 | Pocius |
| 6,039,965 A | 3/2000 | Donlan et al. |
| 6,241,898 B1 | 6/2001 | Wright et al. |
| 6,413,921 B1 | 7/2002 | Childers et al. |
| 2009/0176887 A1 | 7/2009 | Vlasaty et al. |
| 2010/0081607 A1 | 4/2010 | Varineau et al. |
| 2011/0098492 A1 | 4/2011 | Varineau et al. |
| 2013/0053422 A1 | 2/2013 | Edmonds et al. |

FOREIGN PATENT DOCUMENTS

| | | |
|---|---|---|
| CA | 1262084 A | 10/1989 |
| EP | 1454527 A1 | 9/2004 |
| GB | 2138798 A | 10/1984 |

OTHER PUBLICATIONS

"Phenoxyethanol technical datasheet", pp. 1-2 (2000). XP5516990.
Tadashi, et al., "Cosmetics Containing Phenoxyethanol and/or Phenethyl Alcohol", Caplus (1999). XP002237695.
Adkins, et al., "Morphology and Stability o fCO 2 - in-Water Foams with Nonionic Hydrocarbon Surfactants", Langmuir, vol. 26, No. 8, pp. 5335-5348 (2010). XP55115328.

*Primary Examiner* — Raymond Henley, III
(74) *Attorney, Agent, or Firm* — Kenneth Crimaldi

(57) ABSTRACT

An aqueous microbicidal composition having two components. The first component is a nonionic surfactant with structure: $R^1O(CH_2CH(CH_3)O)_5(CH_2CH_2O)_9H$, where $R^1$ is a $C_8$ alkyl group. The second component is phenoxyethanol. The weight ratio of the nonionic surfactant to phenoxyethanol is from 1:1 to 1:18.2766.

10 Claims, No Drawings

MICROBICIDAL COMPOSITION

This invention relates to microbicidal compositions containing 2-phenoxyethanol and a surfactant.

A composition containing 5-chloro-2-methylisothiazolin-3-one, 2-methylisothiazolin-3-one and a nonionic dispersant is disclosed in U.S. Pat. No. 4,295,932. The composition contains a 3:1 mixture of 5-chloro-2-methylisothiazolin-3-one and 2-methylisothiazolin-3-one, and a copolymer of ethylene oxide and propylene oxide which appears to have the same composition as PLURONIC L61 or TERGITOL L61 dispersant. However, there is a need for combinations of microbicides having synergistic activity against various strains of microorganisms to provide effective control of the microorganisms. Moreover, there is a need for such combinations containing lower levels of individual microbicides for environmental and economic benefit. The problem addressed by this invention is to provide such synergistic combinations of microbicides.

STATEMENT OF THE INVENTION

The present invention is directed to a synergistic microbicidal composition comprising: (a) a nonionic surfactant with structure:

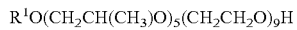
$$R^1O(CH_2CH(CH_3)O)_5(CH_2CH_2O)_9H$$

where $R^1$ is a $C_8$ alkyl group; and (b) phenoxyethanol; wherein a weight ratio of said nonionic surfactant to phenoxyethanol is from 1:1 to 1:18.2766.

The present invention is further directed to a synergistic microbicidal composition comprising: (a) a nonionic surfactant with structure:

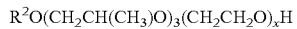
$$R^2O(CH_2CH(CH_3)O)_3(CH_2CH_2O)_xH$$

where $R^2$ is a mixture of $C_8$-$C_{14}$ linear alkyl groups and x is an integer from 5 to 7; and (b) phenoxyethanol; wherein a weight ratio of said nonionic surfactant to phenoxyethanol is from 1:0.1999 to 1:36.5897.

DETAILED DESCRIPTION OF THE INVENTION

"Phenoxyethanol" is 2-phenoxy-1-ethanol (CAS No. 122-99-6). As used herein, the following terms have the designated definitions, unless the context clearly indicates otherwise. The term "microbicide" refers to a compound capable of inhibiting the growth of or controlling the growth of microorganisms; microbicides include bactericides, fungicides and algaecides. The term "microorganism" includes, for example, fungi (such as yeast and mold), bacteria and algae. The following abbreviations are used throughout the specification: ppm=parts per million by weight (weight/weight), mL=milliliter. Unless otherwise specified, temperatures are in degrees centigrade (° C.), references to percentages are percentages by weight (wt %) and amounts and ratios are on an active ingredient basis, i.e., total weight of phenoxyethanol and the nonionic surfactant. Numbers of polymerized units of propylene oxide or ethylene oxide are number averages.

Preferably, the weight ratio of the nonionic surfactant with structure: $R^1O(CH_2CH(CH_3)O)_5(CH_2CH_2O)_9H$, where $R^1$ is a $C_8$ alkyl group, to phenoxyethanol is from 1:1.5992 to 1:18.2766; preferably from 1:1 to 1:2. Preferably, the $C_8$ alkyl group is 2-ethylhexyl. The present invention is further directed to a method for inhibiting the growth of microorganisms in an aqueous medium by adding to said aqueous medium said nonionic surfactant and phenoxyethanol; wherein the weight ratio of the nonionic surfactant to phenoxyethanol is from 1:1 to 1:18.2766. The present invention is further directed to a method for inhibiting the growth of *P. aeruginosa* in an aqueous medium by adding to said aqueous medium said nonionic surfactant and phenoxyethanol; wherein the weight ratio of the nonionic surfactant to phenoxyethanol is from 1:1.5992 to 1:18.2766.

When a nonionic surfactant with structure: $R^2O(CH_2CH(CH_3)O)_3(CH_2CH_2O)_xH$, where $R^2$ is a mixture of $C_8$-$C_{14}$ linear alkyl groups and x is an integer from 5 to 7, is combined with phenoxyethanol, preferably the $C_8$-$C_{14}$ linear alkyl groups comprise from 50 to 85 wt % $C_8$-$C_{10}$ linear alkyl groups and 15 to 50 wt % $C_{12}$-$C_{14}$ linear alkyl groups, preferably from 60 to 75 wt % $C_8$-$C_{10}$ linear alkyl groups and 25 to 40 wt % $C_{12}$-$C_{14}$ linear alkyl groups, preferably about 70 wt % $C_8$-$C_{10}$ linear alkyl groups and about 30 wt % $C_{12}$-$C_{14}$ linear alkyl groups. Preferably, the linear alkyl groups are derived from seed oil. Preferably x is 5 or 7. When x is 5, preferably the weight ratio of the nonionic surfactant to phenoxyethanol is from 1:0.1999 to 1:36.5877. When x is 7, preferably the weight ratio of the nonionic surfactant to phenoxyethanol is from 1:0.7996 to 1:27.4377, preferably from 1:1 to 1:6. The present invention is further directed to a method for inhibiting the growth of microorganisms in an aqueous medium by adding to said aqueous medium said nonionic surfactant and phenoxyethanol; wherein the weight ratio of said nonionic surfactant to phenoxyethanol is from 1:0.1999 to 1:36.5897. The present invention is further directed to a method for inhibiting the growth of *S. aureus* in an aqueous medium by adding to said aqueous medium a surfactant with structure: $R^2O(CH_2CH(CH_3)o)_3(CH_2CH_2O)_5H$, where $R^2$ is a mixture of $C_8$-$C_{14}$ linear alkyl groups, and phenoxyethanol; wherein the weight ratio of the nonionic surfactant to phenoxyethanol is from 1:0.1999 to 1:36.5897. The present invention is further directed to a method for inhibiting the growth of mold, preferably *A. niger*, in an aqueous medium by adding to said aqueous medium a surfactant with structure: $R^2O(CH_2CH(CH_3)o)_3(CH_2CH_2O)_5H$, where $R^2$ is a mixture of $C_8$-$C_{14}$ linear alkyl groups, and phenoxyethanol; wherein the weight ratio of the nonionic surfactant to phenoxyethanol is from 1:0.3998 to 1:13.7006. The present invention is further directed to a method for inhibiting the growth of *S. aureus* in an aqueous medium by adding to said aqueous medium a surfactant with structure: $R^2O(CH_2CH(CH_3)o)_3(CH_2CH_2O)_7H$, where $R^2$ is a mixture of $C_8$-$C_{14}$ linear alkyl groups, and phenoxyethanol; wherein the weight ratio of the nonionic surfactant to phenoxyethanol is from 1:0.7996 to 1:27.4377. In each of the aforementioned methods, the preferred compositions of the linear alkyl groups are as stated earlier in this paragraph.

Preferably, each of the synergistic microbicidal compositions is substantially free of microbicides other than the nonionic surfactant and phenoxyethanol, i.e., it has less than 1 wt % of microbicides other than the nonionic surfactant and phenoxyethanol based on total weight of active ingredients, preferably less than 0.5 wt %, preferably less than 0.2 wt %, preferably less than 0.1 wt %. Preferably, when the nonionic surfactant and phenoxyethanol are added to an aqueous medium, the medium is substantially free of other microbicides, i.e., it has less than 1 wt % of microbicides other than the nonionic surfactant and phenoxyethanol based on total weight of active ingredients, preferably less than 0.5 wt %, preferably less than 0.2 wt %, preferably less than 0.1 wt %.

The compositions of this invention may contain other ingredients, e.g., defoamers and emulsifiers. The microbicidal compositions of the present invention can be used to inhibit the growth of microorganisms or higher forms of aquatic life (such as protozoans, invertebrates, bryozoans, dinoflagellates, crustaceans, mollusks, etc) by introducing a microbicidally effective amount of the compositions into an aqueous medium subject to microbial attack. Suitable aqueous media are found in, for example: industrial process water; electrocoat deposition systems; cooling towers; air washers; gas scrubbers; mineral slurries; wastewater treatment; ornamental fountains; reverse osmosis filtration; ultrafiltration; ballast water; evaporative condensers; heat exchangers; pulp and paper processing fluids and additives; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom and kitchen cleaners; cosmetics; toiletries; shampoos; soaps; personal care products such as wipes, lotions, sunscreen, conditioners, creams, and other leave-on applications; detergents; industrial cleaners; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

The specific amount of the microbicidal compositions of this invention necessary to inhibit or control the growth of microorganisms in an application will vary. Typically, the amount of the composition of the present invention is sufficient to control the growth of microorganisms if it provides from 1,000 to 20,000 ppm (parts per million) active ingredients of the composition. It is preferred that the active ingredients (i.e., nonionic surfactant and phenoxyethanol) of the composition be present in the medium to be treated in an amount of at least 2,000 ppm, preferably at least 3,000 ppm, preferably at least 4,000 ppm. It is preferred that the active ingredients of the composition be present in the locus in an amount of no more than 16,000 ppm, preferably no more than 14,000 ppm, preferably no more than 12,000 ppm, preferably no more than 10,000 ppm, preferably no more than 8,000 ppm, preferably no more than 7,000 ppm. In a method of this invention, a composition is treated to inhibit microbial growth by adding, together or separately, the nonionic surfactant and phenoxyethanol, in amounts that would produce the concentrations indicated above.

EXAMPLES

Surfactants and biocides were evaluated for synergy by determining the synergy index (S.I.) of the combination. Synergy index was calculated based on minimum inhibitory concentrations (MIC) of two antimicrobial compounds (A and B) alone and in combinations. The tests organisms were Gram negative bacteria (*Pseudomonas aeruginosa* ATCC #15442),
Gram positive bacteria (*Staphylococcus aureus* ATCC #6538), yeast (*Candida albicans* ATCC#10203) and mold (*Aspergillus niger* ATCC#16404). Contact time for the bacteria was 24 and 48 hours, yeast was 48 and 72 hrs, and 3 and 7 days for mold. The test was carried out in 96 well microtiter plates.

Surf. A $R^1O(CH_2CH(CH_3)o)_5(CH_2CH_2O)_9H$, where $R^1$ is 2-ethylhexyl

Surf. D $R^2O(CH_2CH(CH_3)o)_3(CH_2CH_2O)_5H$

Surf. E $R^2O(CH_2CH(CH_3)o)_3(CH_2CH_2O)_7H$

In Surf. D and Surf. E, $R^2$ is a mixture of $C_8$-$C_{14}$ linear alkyl groups (70% $C_8$-$C_{10}$ linear alkyl and 30% $C_{12}$-$C_{14}$ linear alkyl)

Inoculums Used

| | Inoculum Size of organisms ( CFU/ml ) | | | |
|---|---|---|---|---|
| Surfactants | *Staphylococcus aureus* ATCC# 6538 | *Pseudomonas aeruginosa* ATCC # 15442 | *Aspergillus niger* ATCC# 16404 | *Candida albicans* ATCC# 10203 |
| Surf. A | 1.156E+06 | 8.134E+07 | 1.156E+06 | 1.156 +06 |
| Surf. D | 1.808E+05 | 1.156E+08 | 1.156E+06 | 5.726E+05 |
| Surf. E | 1.808E+06 | 5.727E+07 | 5.726E+05 | 1.808E+06 |

TABLE 4

Media Used
Media Used for testing

| *Staphylococcus aureus* ATCC# 6538 | *Pseudomonas aeruginosa* ATCC # 15442 | *Aspergillus niger* ATCC# 16404 | *Candida albicans* ATCC#10203 |
|---|---|---|---|
| 10% Tryptic soy broth | 10% Tryptic soy broth | Potato dextrose broth | Potato dextrose broth |

The pH of the Triptic soy broth was 7.3 and the Potato dextrose broth was 5.1.

The test results for demonstration of synergy of the MIC combinations are shown in the tables below. Each table shows the results for combinations of two components against the microorganisms tested with incubation times; the end-point activity in ppm measured by the MIC for compound A alone (CA), for component B alone (CB), and the mixture (Ca) and (Cb); the calculated SI value; and the range of synergistic ratios for each combination tested. SI is calculated as follows:

$$Ca/CA + Cb/CB = \text{Synergy Index (``SI'')}$$

Wherein:
CA=concentration of compound A in ppm, acting alone, which produced an end point (MIC of Compound A).
Ca=concentration of compound A in ppm, in the mixture, which produced an end point.
CB=concentration of compound B in ppm, acting alone, which produced an end point (MIC of Compound B).
Cb=concentration of compound B in ppm, in the mixture, which produced an end point.

When the sum of Ca/CA and Cb/CB is greater than one, antagonism is indicated. When the sum is equal to one, additivity is indicated, and when less than one, synergism is demonstrated.

The ratio ranges at which phenoxyethanol and the surfactants were tested are as summarized in the following tables:

| Phenoxyethanol with Surf. A | | | | |
|---|---|---|---|---|
| Organism | ATCC# | From | To | Ratio Range |
| S. aureus | 6538 | 2.0:20,000 | 10,000:218.75 | 1:0.0001-1:45.7143 |
| A. niger | 16404 | 0.2:20,000 | 1,000:218.75 | 1:0.00001-1:4.5714 |
| C. albicans | 10203 | 0.2:20,000 | 1,000:218.75 | 1:0.00001-1:4.5714 |
| Ps. aeruginosa | 15442 | 2.0:20,000 | 10,000:218.75 | 1:0.0001-1:45.7143 |

| Phenoxyethanol with Surf. E | | | | |
|---|---|---|---|---|
| Organism | ATCC# | From | To | Ratio Range |
| S. aureus | 6538 | 2.0:20,000 | 10,000:218.75 | 1:0.0001-1:45.7143 |
| A. niger | 16404 | 0.2:20,000 | 1,000:218.75 | 1:0.00001-1:4.5714 |
| C. albicans | 10203 | 0.2:20,000 | 1,000:218.75 | 1:0.00001-1:4.5714 |
| Ps. aeruginosa | 15442 | 2.0:20,000 | 10,000:218.75 | 1:0.0001-1:45.7143 |

| Phenoxyethanol with Surf. D | | | | |
|---|---|---|---|---|
| S. aureus | ATCC# | From | To | Ratio Range |
| A. niger | 6538 | 2.0:20,000 | 10,000:218.75 | 1:0.0001-1:45.7143 |
| C. albicans | 16404 | 2.0:20,000 | 10,000:218.75 | 1:0.0001-1:45.7143 |
| Ps. aeruginosa | 10203 | 2.0:20,000 | 10,000:218.75 | 1:0.0001-1:45.7143 |
| S. aureus | 15442 | 2.0:20,000 | 10,000:218.75 | 1:0.0001-1:45.7143 |

A: Surf. A
B: Phenoxyethanol

| A. niger | ATCC#16404 | No Synergy |
|---|---|---|
| C. albicans | ATCC#10203 | No Synergy |

A: Surf. A
B: Phenoxyethanol
Media: 1/10 TSB
Inoculum size: 8.134E+07CFU/ml

| | PPM AI MIC Values (24 hrs) | | | | | |
|---|---|---|---|---|---|---|
| Test | Alone | | Combination | | | Ratio |
| Organism | CA | CB | Ca | Cb | S.I. | (Ca:Cb) |
| Ps. aeruginosa ATCC#15442 | >20000 | 4997 | 2500 | 3998 | <0.93 | 1:1.5992 |
| | >20000 | 4997 | 1750 | 3998 | <0.89 | 1:2.2846 |
| | >20000 | 4997 | 875 | 3998 | <0.84 | 1:4.5691 |
| | >20000 | 4997 | 437.5 | 3998 | <0.82 | 1:9.1383 |
| | >20000 | 4997 | 218.75 | 3998 | <0.81 | 1:18.2766 |

A: Surf. A
B: Phenoxyethanol
Media: 1/10 TSB
Inoculum size: 1.156E-+06CFU/ml

| | PPM AI MIC Values (24 hrs) | | | | | |
|---|---|---|---|---|---|---|
| Test | Alone | | Combination | | | Ratio |
| Organism | CA | CB | Ca | Cb | S.I. | (Ca:Cb) |
| S. aureus ATCC# 6538 | >20000 | 8000 | 5000 | 5000 | <0.88 | 1:1.0000 |
| | >20000 | 8000 | 2500 | 5000 | <0.75 | 1:2.0000 |
| | >20000 | 8000 | 1750 | 5000 | <0.71 | 1:2.8571 |

-continued

| | PPM AI MIC Values (24 hrs) | | | | | |
|---|---|---|---|---|---|---|
| Test | Alone | | Combination | | | Ratio |
| Organism | CA | CB | Ca | Cb | S.I. | (Ca:Cb) |
| | >20000 | 8000 | 1750 | 6000 | <0.84 | 1:3.4286 |
| | >20000 | 8000 | 875 | 6000 | <0.79 | 1:6.8571 |

A: Surf. D
B: Phenoxyethanol
Media: PDB
Inoculum size: 1.156E+06

| | PPM AI MIC Values (3rd day) | | | | | |
|---|---|---|---|---|---|---|
| Test | Alone | | Combination | | | Ratio |
| Organism | CA | CB | Ca | Cb | S.I. | (Ca:Cb) |
| A. niger ATCC#16404 | >20000 | 3998 | 5000 | 1999 | <0.75 | 1:0.3998 |
| | >20000 | 3998 | 2500 | 1000 | <0.38 | 1:0.4000 |
| | >20000 | 3998 | 2500 | 1999 | <0.63 | 1:0.7996 |
| | >20000 | 3998 | 2500 | 2997 | <0.87 | 1:1.1988 |
| | >20000 | 3998 | 1750 | 1999 | <0.59 | 1:1.1423 |
| | >20000 | 3998 | 875 | 1999 | <0.54 | 1:2.2846 |
| | >20000 | 3998 | 437.5 | 2997 | <0.77 | 1:6.8503 |
| | >20000 | 3998 | 218.75 | 2997 | <0.76 | 1:13.7006 |

A: Surf. D
B: Phenoxyethanol
Media: PDB
Inoculum size: 5.726E+05CFU/ml

| | PPM AI MIC Values (48 hrs) | | | | | |
|---|---|---|---|---|---|---|
| Test | Alone | | Combination | | | Ratio |
| Organism | CA | CB | Ca | Cb | S.I. | (Ca:Cb) |
| C. albicans ATCC#10203 | >20000 | 3998 | 2500 | 1999 | <0.63 | 1:0.7996 |
| | >20000 | 3998 | 2500 | 2997 | <0.87 | 1:1.1988 |
| | >20000 | 3998 | 437.5 | 1999 | <0.52 | 1:4.5691 |

A: Surf. D
B: Phenoxyethanol
Media: 1/10 TSB
Inoculum size: 1.16E+05CFU/ml

| PPM AI MIC Values (24 hrs) | | | | | |
|---|---|---|---|---|---|
| Test | Alone | | Combination | | Ratio |
| Organism | CA | CB | Ca | Cb | S.I. | (Ca:Cb) |
| Ps. aeruginosa | >20000 | 3998 | 2500 | 2997 | <0.87 | 1:1.1988 |
| ATCC#15442 | >20000 | 3998 | 1750 | 2997 | <0.84 | 1:1.7126 |
| | >20000 | 3998 | 875 | 2997 | <0.79 | 1:3.4251 |
| | >20000 | 3998 | 437.5 | 2997 | <0.77 | 1:6.8503 |
| | >20000 | 3998 | 218.75 | 1999 | <0.51 | 1:9.1383 |

A: Surf. D
B: Phenoxyethanol
Media: 1/10 TSB
Inoculum size: 1.808E+05

| PPM AI MIC Values (24 hrs) | | | | | |
|---|---|---|---|---|---|
| Test | Alone | | Combination | | Ratio |
| Organism | CA | CB | Ca | Cb | S.I. | (Ca:Cb) |
| S. aureus | >20000 | 9999 | 10000 | 1999 | <0.70 | 1:0.1999 |
| ATCC# 6538 | >20000 | 9999 | 10000 | 2997 | <0.80 | 1:0.2997 |
| | >20000 | 9999 | 10000 | 3998 | <0.90 | 1:0.3998 |
| | >20000 | 9999 | 5000 | 6002 | <0.85 | 1:1.2004 |
| | >20000 | 9999 | 5000 | 4997 | <0.75 | 1:0.9994 |
| | >20000 | 9999 | 5000 | 3998 | <0.65 | 1:0.7996 |
| | >20000 | 9999 | 5000 | 2997 | <0.55 | 1:0.5994 |
| | >20000 | 9999 | 2500 | 8004 | <0.93 | 1:3.2016 |
| | >20000 | 9999 | 1750 | 8004 | <0.89 | 1:4.5737 |
| | >20000 | 9999 | 1750 | 6002 | <0.69 | 1:3.4297 |
| | >20000 | 9999 | 1750 | 4997 | <0.59 | 1:2.8554 |
| | >20000 | 9999 | 1750 | 3998 | <0.49 | 1:2.2846 |
| | >20000 | 9999 | 1750 | 2997 | <0.39 | 1:1.7126 |
| | >20000 | 9999 | 1750 | 1999 | <0.29 | 1:1.1423 |
| | >20000 | 9999 | 875 | 8004 | <0.84 | 1:9.1474 |
| | >20000 | 9999 | 875 | 6002 | <0.64 | 1:6.8594 |
| | >20000 | 9999 | 875 | 4997 | <0.54 | 1:5.7109 |
| | >20000 | 9999 | 875 | 3998 | <0.44 | 1:4.5691 |
| | >20000 | 9999 | 875 | 2997 | <0.34 | 1:3.4251 |
| | >20000 | 9999 | 437.5 | 2997 | <0.32 | 1:6.8503 |
| | >20000 | 9999 | 437.5 | 3998 | <0.42 | 1:9.1383 |
| | >20000 | 9999 | 437.5 | 4997 | <0.52 | 1:11.4217 |
| | >20000 | 9999 | 437.5 | 6002 | <0.62 | 1:13.7189 |
| | >20000 | 9999 | 437.5 | 8004 | <0.82 | 1:18.2949 |
| | >20000 | 9999 | 218.75 | 4997 | <0.51 | 1:22.8434 |
| | >20000 | 9999 | 218.75 | 6002 | <0.61 | 1:27.4377 |
| | >20000 | 9999 | 218.75 | 8004 | <0.81 | 1:36.5897 |

A: Surf. E
B: Phenoxyethanol

| A. niger | ATCC#16404 | No Synergy |
|---|---|---|
| C. albicans | ATCC#10203 | No Synergy |

A: Surf. E
B: Phenoxyethanol
Media: 1/10 TSB
Inoculum size: 5.727E+07CFU/ml

| PPM AI MIC Values (24 hrs) | | | | | |
|---|---|---|---|---|---|
| Test | Alone | | Combination | | Ratio |
| Organism | CA | CB | Ca | Cb | S.I. | (Ca:Cb) |
| Ps. aeruginosa | >20000 | 3998 | 2500 | 2997 | 0.87 | 1:1.1988 |
| ATCC#15442 | >20000 | 3998 | 1750 | 2997 | 0.84 | 1:1.7126 |
| | >20000 | 3998 | 875 | 2997 | 0.79 | 1:3.4251 |
| | >20000 | 3998 | 437.5 | 2997 | 0.77 | 1:6.8503 |

A: Surf. E
B: Phenoxyethanol
Media: 1/10 TSB
Inoculum size: 1.808E+06CFU/ml

| PPM AI MIC Values (24 hrs) | | | | | |
|---|---|---|---|---|---|
| Test | Alone | | Combination | | Ratio |
| Organism | CA | CB | Ca | Cb | S.I. | (Ca:Cb) |
| S. aureus | >20000 | 8004 | 5000 | 3998 | 0.75 | 1:0.7996 |
| ATCC# 6538 | >20000 | 8004 | 5000 | 4997 | 0.87 | 1:0.9994 |
| | >20000 | 8004 | 2500 | 2997 | 0.50 | 1:1.1988 |
| | >20000 | 8004 | 2500 | 3998 | 0.62 | 1:1.5992 |
| | >20000 | 8004 | 2500 | 4997 | 0.75 | 1:1.9988 |
| | >20000 | 8004 | 2500 | 6002 | 0.87 | 1:2.4008 |
| | >20000 | 8004 | 1750 | 3998 | 0.59 | 1:2.2846 |
| | >20000 | 8004 | 1750 | 4997 | 0.71 | 1:2.8554 |
| | >20000 | 8004 | 1750 | 6002 | 0.84 | 1:3.4297 |
| | >20000 | 8004 | 875 | 3998 | 0.54 | 1:4.5691 |
| | >20000 | 8004 | 875 | 4997 | 0.67 | 1:5.7109 |
| | >20000 | 8004 | 875 | 6002 | 0.79 | 1:6.8594 |
| | >20000 | 8004 | 437.5 | 2997 | 0.40 | 1:6.8503 |
| | >20000 | 8004 | 437.5 | 3998 | 0.52 | 1:9.1383 |
| | >20000 | 8004 | 437.5 | 4997 | 0.65 | 1:11.4217 |
| | >20000 | 8004 | 437.5 | 6002 | 0.77 | 1:13.7189 |
| | >20000 | 8004 | 218.75 | 4997 | 0.64 | 1:22.8434 |
| | >20000 | 8004 | 218.75 | 6002 | 0.76 | 1:27.4377 |

The following biocides had no synergy against any organism tested when paired with the following surfactants:

Surf. A

Sodium Benzoate, Tris Nitro

Surf. E

DMDMH

Surf. D

CS-1246, OPP, DMDMH

In the following combinations, the ratio of surfactant to biocide where synergy was observed were not commercially relevant, i.e., a ratio of 1:0.2 or greater (less biocide relative to surfactant). At these ratios, the biocide levels in a formulated product would be too low to be practical:

Surf. A

DIDAC, IPBC

Surf. E

CMIT/MIT, IPBC, OIT, TTPC, WSCP

Surf. D

CMIT/MIT, OIT, DIDAC
(MBIT, IPBC, WSCP were synergistic only at 1:0.05 or worse except for one data point)

Stability Testing

A solution of phenoxyethanol in 70% (v/v) isopropanol was made and diluted with surfactant to give the desired ratios of biocide to surfactant. Additional 70% isopropanol was added as needed to give a 33 wt % solution of phenoxyethanol. The samples were split into three vials. One vial was stored at room temperature, one was stored at 40 C and one was stored at 50 C. Samples were evaluated after a week to determine stability. Samples that were cloudy or highly discolored were determined to be unstable. In the data tables, a dash indicates that the formulation was stable.

Stability Data - 33% Phenoxyethanol (PE) in combination with Surfactants - Day 1

| | | Temperature | | |
|---|---|---|---|---|
| Surfactant | PE:Surfactant | Room Temperature | 40° C. | 50° C. |
| Surf. D | 1:1 | — | — | — |
| | 1:6 | Cloudy | — | — |
| | 1:27 | Slightly cloudy | — | — |
| Surf. E | 1:1 | — | — | — |
| | 1:6 | — | — | — |
| | 1:27 | Slightly cloudy | — | — |
| Surf. A | 1:1 | — | — | — |
| | 1:2 | — | — | — |
| Surf. B | 1:1 | — | — | — |
| | 1:2 | — | — | — |
| POLYSORBATE 20 | 1:1 | — | — | — |
| | 1:2 | — | — | — |
| | 1:6 | — | — | — |
| | 1:27 | — | — | — |
| Disodium cocoamphodiacetate | 1:1 | Cloudy | Cloudy | Cloudy |
| | 1:2 | — | — | — |
| | 1:6 | — | — | — |
| | 1:27 | Slightly cloudy | — | — |
| TERGITOL L-62 | 1:1 | — | — | — |
| | 1:2 | — | — | — |
| | 1:6 | Cloudy | — | — |
| | 1:27 | Cloudy | — | — |
| TERGITOL 81 | 1:1 | — | — | — |
| | 1:2 | Cloudy | — | — |
| | 1:6 | Cloudy | — | — |
| | 1:27 | Cloudy | — | — |
| TERGITOL 15-S-7 | 1:1 | — | — | — |
| | 1:2 | — | — | — |
| | 1:6 | — | — | — |
| | 1:27 | Cloudy | — | — |

* Surf. B is $R^1O(CH_2CH(CH_3)O)_5(CH_2CH_2O)_6H$, where $R^1$ is 2-ethylhexyl

Stability Data - 33% Phenoxyethanol in combination with Surfactants - Day 2

| | | Temperature | | |
|---|---|---|---|---|
| Surfactant | PE:Surfactant | Room Temperature | 40° C. | 50° C. |
| Surf. D | 1:1 | — | — | — |
| | 1:6 | Cloudy | — | — |
| | 1:27 | Slightly cloudy | — | — |
| Surf. E | 1:1 | — | — | — |
| | 1:6 | — | — | — |
| | 1:27 | Slightly cloudy | — | — |
| Surf. A | 1:1 | — | — | — |
| | 1:2 | — | — | — |
| Surf. B | 1:1 | — | — | — |
| | 1:2 | — | — | — |
| POLYSORBATE 20 | 1:1 | — | — | — |
| | 1:2 | — | — | — |
| | 1:6 | — | — | — |
| | 1:27 | — | Slightly cloudy | Slightly cloudy |
| Disodium cocoamphodiacetate | 1:1 | Cloudy | Cloudy | Cloudy |
| | 1:2 | — | — | — |
| | 1:6 | — | — | — |
| | 1:27 | Slightly cloudy | — | — |
| TERGITOL L-62 | 1:1 | — | — | — |
| | 1:2 | — | — | — |
| | 1:6 | Cloudy | — | — |
| | 1:27 | Cloudy | — | — |
| TERGITOL 81 | 1:1 | — | — | — |
| | 1:2 | Cloudy | — | — |
| | 1:6 | Cloudy | — | — |
| | 1:27 | Cloudy | — | — |
| TERGITOL 15-S-7 | 1:1 | — | — | — |
| | 1:2 | — | — | — |
| | 1:6 | — | — | — |
| | 1:27 | Cloudy | — | — |

Stability Data - 33% Phenoxyethanol in combination with Surfactants - Day 7

| | | Temperature | | |
|---|---|---|---|---|
| Surfactant | PE:Surfactant | Room Temperature | 40° C. | 50° C. |
| Surf. D | 1:1 | — | — | — |
| | 1:6 | Cloudy | — | — |
| | 1:27 | Slightly cloudy | — | — |
| Surf. E | 1:1 | — | — | — |
| | 1:6 | — | — | — |
| | 1:27 | Slightly cloudy | — | — |
| Surf. A | 1:1 | — | — | — |
| | 1:2 | — | — | — |
| Surf. B | 1:1 | — | — | — |
| | 1:2 | — | — | — |
| POLYSORBATE 20 | 1:1 | — | — | — |
| | 1:2 | — | — | — |
| | 1:6 | — | — | — |
| | 1:27 | — | Slightly cloudy | Slightly cloudy |
| Disodium cocoamphodiacetate | 1:1 | Cloudy | Cloudy | Cloudy |
| | 1:2 | — | — | — |
| | 1:6 | — | — | — |
| | 1:27 | Slightly cloudy | — | — |
| TERGITOL L-62 | 1:1 | — | — | — |
| | 1:2 | — | — | — |
| | 1:6 | Cloudy | — | — |
| | 1:27 | Cloudy | — | — |
| TERGITOL 81 | 1:1 | — | — | — |
| | 1:2 | Cloudy | — | — |
| | 1:6 | Cloudy | — | — |
| | 1:27 | Cloudy | — | — |
| TERGITOL 15-S-7 | 1:1 | — | — | — |
| | 1:2 | — | — | — |
| | 1:6 | — | — | — |
| | 1:27 | Cloudy | — | — |

The invention claimed is:

1. A synergistic microbicidal composition comprising: (a) a nonionic surfactant with structure:

$$R^1O(CH_2CH(CH_3)o)_5(CH_2CH_2O)_9H$$

where $R^1$ is a $C_8$ alkyl group; and (b) phenoxyethanol; wherein a weight ratio of said nonionic surfactant to phenoxyethanol is from 1:1 to 1:18.2766.

2. The synergistic microbicidal composition of claim 1 in which said $C_8$ alkyl group is 2-ethylhexyl.

3. A method for inhibiting the growth of microorganisms in an aqueous medium; said method comprising adding to said aqueous medium: (a) a nonionic surfactant with structure:

$$R^1O(CH_2CH(CH_3)o)_5(CH_2CH_2O)_9H$$

where $R^1$ is a $C_8$ alkyl group; and (b) phenoxyethanol; wherein a weight ratio of said nonionic surfactant to phenoxyethanol is from 1:1 to 1:18.2766.

4. The method of claim 3 in which said $C_8$ alkyl group is 2-ethylhexyl.

5. A synergistic microbicidal composition comprising: (a) a nonionic surfactant with structure:

$$R^2O(CH_2CH(CH_3)o)_3(CH_2CH_2O)_xH$$

where $R^2$ is a mixture of $C_8$-$C_{14}$ linear alkyl groups and x is an integer from 5 to 7; and (b) phenoxyethanol; wherein a weight ratio of said nonionic surfactant to phenoxyethanol is from 1:0.1999 to 1:36.5897.

6. The synergistic microbicidal composition of claim 5 in which said mixture of $C_8$-$C_{14}$ linear alkyl groups comprises from 60 to 75 wt % $C_8$-$C_{10}$ linear alkyl groups and 25 to 40 wt % $C_{12}$-$C_{14}$ linear alkyl groups.

7. The synergistic microbicidal composition of claim 6 in which x is 5.

8. The synergistic microbicidal composition of claim 6 in which x is 7 and said weight ratio is 1:0.7996 to 1:27.4377.

9. A method for inhibiting the growth of microorganisms in an aqueous medium; said method comprising adding to said aqueous medium: (a) a nonionic surfactant with structure:

$$R^2O(CH_2CH(CH_3)o)_3(CH_2CH_2O)_xH$$

where $R^2$ is a mixture of $C_8$-$C_{14}$ linear alkyl groups and x is an integer from 5 to 7; and (b) phenoxyethanol; wherein a weight ratio of said nonionic surfactant to phenoxyethanol is from 1:0.1999 to 1:36.5897.

10. The method of claim 9 in which. said mixture of $C_8$-$C_{14}$ linear alkyl groups comprises from 60 to 75 wt % $C_8$-$C_{10}$ linear alkyl groups and 25 to 40 wt % $C_{12}$-$C_{14}$ linear alkyl groups.

* * * * *